United States Patent
Orita et al.

(10) Patent No.: US 8,143,427 B2
(45) Date of Patent: Mar. 27, 2012

(54) METHOD FOR PRODUCING AMINOACETYLPYRROLIDINE-CARBONITRILE DERIVATIVE

(75) Inventors: Kazuo Orita, Tochigi (JP); Takayuki Gotoh, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/450,305

(22) PCT Filed: Mar. 21, 2008

(86) PCT No.: PCT/JP2008/055202
§ 371 (c)(1),
(2), (4) Date: Sep. 21, 2009

(87) PCT Pub. No.: WO2008/114857
PCT Pub. Date: Sep. 25, 2008

(65) Prior Publication Data
US 2010/0099892 A1    Apr. 22, 2010

(30) Foreign Application Priority Data
Mar. 22, 2007    (JP) .............................. P2007 073904

(51) Int. Cl.
C07D 207/04    (2006.01)
(52) U.S. Cl. ...................................................... 548/537
(58) Field of Classification Search ....................... None
See application file for complete search history.

(56) References Cited

U.S. PATENT DOCUMENTS

| | | | |
|---|---|---|---|
| 5,939,560 A | 8/1999 | Jenkins et al. |
| 5,965,764 A | 10/1999 | Matsuoka et al. |
| 6,166,063 A | 12/2000 | Villhauer |
| 6,303,661 B1 | 10/2001 | Demuth et al. |
| 6,432,969 B1 | 8/2002 | Villhauer |
| 6,849,622 B2 | 2/2005 | Yasuda et al. |
| 7,132,443 B2 | 11/2006 | Haffner et al. |
| 7,138,397 B2 | 11/2006 | Yasuda et al. |
| 7,160,877 B2 | 1/2007 | Yasuda et al. |
| 7,183,290 B2 | 2/2007 | Haffner et al. |
| 7,196,201 B2 | 3/2007 | Haffner et al. |
| 7,332,487 B2 | 2/2008 | Yasuda et al. |
| 7,514,571 B2 | 4/2009 | Fukuda et al. |
| 7,560,569 B2 | 7/2009 | Fukuda et al. |
| 7,666,869 B2 | 2/2010 | Yasuda et al. |
| 7,754,757 B2 | 7/2010 | Fukuda et al. |
| 2001/0025023 A1 | 9/2001 | Carr |
| 2001/0031780 A1 | 10/2001 | Kanstrup et al. |
| 2002/0006899 A1 | 1/2002 | Pospisilik et al. |
| 2002/0019339 A1 | 2/2002 | Naughton |
| 2002/0019411 A1 | 2/2002 | Robl et al. |
| 2002/0037829 A1 | 3/2002 | Aronson et al. |
| 2002/0103384 A1 | 8/2002 | Kanstrup et al. |
| 2002/0110560 A1 | 8/2002 | Demuth et al. |
| 2003/0100563 A1 | 5/2003 | Edmondson et al. |
| 2003/0105077 A1 | 6/2003 | Kanstrup et al. |
| 2003/0176357 A1 | 9/2003 | Pospisilik et al. |
| 2003/0225102 A1 | 12/2003 | Sankaranarayanan |
| 2004/0017848 A1 | 1/2004 | Doan et al. |
| 2004/0063935 A1 | 4/2004 | Yasuda et al. |
| 2004/0072892 A1 | 4/2004 | Fukushima et al. |
| 2004/0082607 A1 | 4/2004 | Oi et al. |

(Continued)

FOREIGN PATENT DOCUMENTS

EP    1333025 A1 *    8/2003
(Continued)

OTHER PUBLICATIONS

International Search Report issued May 13, 2008 with Written Opinion in International (PCT) Application No. PCT/JP2008/055202 (with English translation).

(Continued)

*Primary Examiner* — Kamal Saeed
*Assistant Examiner* — Nyeemah A Grazier
(74) *Attorney, Agent, or Firm* — Wenderoth, Lind & Ponack, L.L.P.

(57) ABSTRACT

It is to provide a method for efficiently producing an aminoacetylpyrrolidinecarbonitrile derivative which is useful as a DPP-IV inhibitor. It is a method for producing an aminoacetylpyrrolidinecarbonitrile derivative represented by the formula (2):

[Chem. 2]

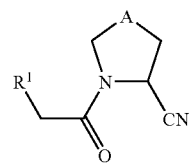

(2)

(in the formula, A and $R^1$ are as defined in the following), comprising allowing an acid to act on an aminoacetylpyrrolidinecarboxamide derivative represented by the formula (1):

[Chem. 1]

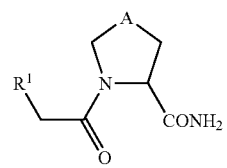

(1)

(in the formula, A represents $CH_2$, $CHF$ or $CF_2$; and $R^1$ represents a secondary amino group which may be substituted), and then allowing a dehydrating agent to act thereon.

10 Claims, No Drawings

U.S. PATENT DOCUMENTS

| | | |
|---|---|---|
| 2004/0106655 A1 | 6/2004 | Kitajima et al. |
| 2004/0106802 A1 | 6/2004 | Sankaranarayanan |
| 2004/0121964 A1 | 6/2004 | Madar et al. |
| 2004/0152745 A1 | 8/2004 | Jackson et al. |
| 2004/0167133 A1 | 8/2004 | Edmondson et al. |
| 2004/0167341 A1 | 8/2004 | Haffner et al. |
| 2004/0176428 A1 | 9/2004 | Edmondson et al. |
| 2004/0229926 A1 | 11/2004 | Yasuda et al. |
| 2004/0242636 A1 | 12/2004 | Haffner et al. |
| 2005/0054678 A1 | 3/2005 | Yasuda et al. |
| 2005/0070719 A1 | 3/2005 | Belyakov et al. |
| 2005/0107308 A1 | 5/2005 | Pospisilik et al. |
| 2005/0107309 A1 | 5/2005 | Demuth et al. |
| 2005/0130981 A1 | 6/2005 | Aranyl et al. |
| 2005/0148606 A1 | 7/2005 | Kanstrup et al. |
| 2005/0153973 A1 | 7/2005 | Aranyl et al. |
| 2005/0164989 A1 | 7/2005 | Abe et al. |
| 2005/0176771 A1 | 8/2005 | Hayakawa et al. |
| 2005/0245538 A1 | 11/2005 | Kitajima et al. |
| 2005/0266080 A1 | 12/2005 | Desai et al. |
| 2006/0142585 A1 | 6/2006 | Thomas et al. |
| 2006/0173056 A1 | 8/2006 | Kitajima et al. |
| 2006/0210627 A1 | 9/2006 | Pfeffer et al. |
| 2006/0241146 A1 | 10/2006 | Yasuda et al. |
| 2006/0270679 A1 | 11/2006 | Edmondson et al. |
| 2007/0112059 A1 | 5/2007 | Fukushima et al. |
| 2007/0112205 A1 | 5/2007 | Fukushima et al. |
| 2007/0167501 A1 | 7/2007 | Fukuda et al. |
| 2007/0265320 A1 | 11/2007 | Fukuda et al. |
| 2008/0038341 A1 | 2/2008 | Kowalski et al. |
| 2008/0050443 A1 | 2/2008 | Kowalski et al. |
| 2008/0146818 A1 | 6/2008 | Fukuda et al. |
| 2009/0048454 A1 | 2/2009 | Asahina et al. |

FOREIGN PATENT DOCUMENTS

| | | |
|---|---|---|
| JP | 09-509921 | 10/1997 |
| JP | 11-322701 | 11/1999 |
| JP | 11322701 A * | 11/1999 |
| JP | 2000-511559 | 9/2000 |
| JP | 2002-531547 | 9/2002 |
| JP | 2002-356471 | 12/2002 |
| JP | 2002-356472 | 12/2002 |
| JP | 2003-520849 | 7/2003 |
| JP | 2003-531118 | 10/2003 |
| JP | 2003-535034 | 11/2003 |
| JP | 2004-002367 | 1/2004 |
| JP | 2004-002368 | 1/2004 |
| JP | 2004-026820 | 1/2004 |
| JP | 2004-503531 | 2/2004 |
| JP | 2005-500321 | 1/2005 |
| JP | 2005-529078 | 9/2005 |
| JP | 2005-532369 | 10/2005 |
| JP | 2006-160733 | 6/2006 |
| JP | 2007-518760 | 7/2007 |
| JP | 2008-501025 | 1/2008 |
| JP | 2008-510764 | 4/2008 |
| JP | 2008-527004 | 7/2008 |
| JP | 2008-239543 | 10/2008 |
| JP | 2008-290969 | 12/2008 |
| JP | 2008-543773 | 12/2008 |
| JP | 2009-114127 | 5/2009 |
| JP | 2010-70454 | 4/2010 |
| WO | 95/015309 | 6/1995 |
| WO | 97/040832 | 11/1997 |
| WO | 98/19998 | 5/1998 |
| WO | 2000/034241 | 6/2000 |
| WO | 01/34594 | 5/2001 |
| WO | 01/055105 | 8/2001 |
| WO | 01/062266 | 8/2001 |
| WO | 01/68603 | 9/2001 |
| WO | 01/96295 | 12/2001 |
| WO | 02/014271 | 2/2002 |
| WO | 02/030890 | 4/2002 |
| WO | 02/30891 | 4/2002 |
| WO | 02/38541 | 5/2002 |
| WO | 02/062764 | 8/2002 |
| WO | 03/000180 | 1/2003 |
| WO | 03/002530 | 1/2003 |
| WO | 03/002531 | 1/2003 |
| WO | 03/002553 | 1/2003 |
| WO | 03/004496 | 1/2003 |
| WO | 03/004498 | 1/2003 |
| WO | 03/015775 | 2/2003 |
| WO | 03/017936 | 3/2003 |
| WO | 03/057144 | 7/2003 |
| WO | 03/057666 | 7/2003 |
| WO | 03/074500 | 9/2003 |
| WO | 03/080633 | 10/2003 |
| WO | 03/084940 | 10/2003 |
| WO | 03/095425 | 11/2003 |
| WO | 03/106456 | 12/2003 |
| WO | 2004/007446 | 1/2004 |
| WO | 2004/009544 | 1/2004 |
| WO | 2004/026822 | 4/2004 |
| WO | 2004/099185 | 11/2004 |
| WO | 2005/067976 | 7/2005 |
| WO | 2005/075421 | 8/2005 |
| WO | 2005/077900 | 8/2005 |
| WO | 2005/082847 | 9/2005 |
| WO | 2005/117841 | 12/2005 |
| WO | 2006/021455 | 3/2006 |
| WO | 2006/040625 | 4/2006 |
| WO | 2006/043595 | 4/2006 |
| WO | 2006/078593 | 7/2006 |
| WO | 2006/135723 | 12/2006 |
| WO | 2007/102286 | 9/2007 |
| WO | 2008/096841 | 8/2008 |
| WO | 2010/016584 | 2/2010 |
| WO | 2010/018866 | 2/2010 |
| WO | 2010/032723 | 3/2010 |

OTHER PUBLICATIONS

International Search Report issued Mar. 15, 2005 with Written Opinion in International (PCT) Application No. PCT/JP2005/001377 (with English translation).

Japanese Office Action issued Jan. 9, 2007 in Japanese Application No. 2005-517671 (with English translation).

U.S. Office Action issued Apr. 3, 2009 in U.S. Appl. No. 10/588,660.

U.S. Office Action issued Oct. 20, 2008 in U.S. Appl. No. 10/588,660.

New Zealand Office Action issued Feb. 12, 2009 in New Zealand Patent Application No. 548440.

Australian Office Action issued Oct. 9, 2007 in Australian Application No. 2005210285.

Chinese Office Action issued Oct. 17, 2008 in Chinese Application No. 200580004191.8 (English Translation only).

Chinese Office Action issued Jun. 5, 2009 in Chinese Application No. 200580004191.8 (English translation only).

Supplementary European Search Report issued Aug. 23, 2007 in European Application No. 05 70 4327.

International Search Report issued Mar. 29, 2005, International Preliminary Report on Patentability issued Sep. 19, 2006 with Written Opinion in International (PCT) Application No. PCT/JP2005/002389 (with English translation).

U.S. Office Action issued Oct. 15, 2008 in U.S. Appl. No. 10/590,111.

Chinese Office Action issued Aug. 8, 2008 in Chinese Application No. 200580005175.0 (English translation only).

International Search Report issued May 10, 2005, International Preliminary Report on Patentability issued Sep. 19, 2006 with Written Opinion in International (PCT) Application No. PCT/JP2005/002806 (with English translation).

U.S. Office Action issued Dec. 21, 2007 in U.S. Appl. No. 10/590,871.

U.S. Office Action issued Aug. 22, 2008 in U.S. Appl. No. 10/590,871.

International Search Report issued May 1, 2007, International Preliminary Report on Patentability issued Sep. 9, 2008 with Written Opinion in International (PCT) Application No. PCT/JP2007/051768 (with English translation).

International Search Report issued Mar. 4, 2008 with Written Opinion in International (PCT) Application No. PCT/JP2008/052096 (with English translation).

C. F. Deacon, et al., "Glucagon-like peptide 1 undergoes differential tissue-specific metabolism in the anesthetized pig", American Journal of Physiology, 1996, vol. 271, pp. E458-E464.

L.B. Knudsen, et al., "Glucagon-like peptide-1-(9-36) amide is a major metabolite of glucagon-like peptide-1-(7-36) amide after in vivo administration to dogs, and it acts as an antagonist on the pancreatic receptor", European Journal of Pharmacology, 1996, vol. 318, pp. 429-435.

E.G. Siegel, et al., "Comparison of the effect of GIP and GLP-1 (7-36amide) on insulin release from rat pancreatic islets", European Journal of Clinical Investigation, 1992, vol. 22, pp. 154-157.

B. Kreymann, et al., "Glucagon-Like Peptide-1 7-36: A Physiological Incretin in Man", The Lancet, 1987, vol. 2, pp. 1300-1303.

H. Fehmann, et al., "Insulinotropic Hormone Glucagon-like Peptide-I(7-37) Stimulation of Proinsulin Gene Expression and Proinsulin Biosynthesis in Insulinoma βTC-1 Cells", Endocrinology, 1992, vol. 130, No. 1, pp. 159-166.

J. Buteau, et al., "Glucagon-like peptide-1 promotes DNA synthesis, activates phosphatidylinositol 3-kinase and increases transcription factor pancreatic and duodenal homeobox gene 1 (PDX-1) DNA binding activity in beta (INS-1)-cells", Diabetologia, 1999, vol. 42, pp. 856-864.

J. M. Egan, et al., "Glucagon-Like Peptide-1(7-36) Amide (GLP-1) Enhances Insulin-Stimulated Glucose Metabolism in 3T3-L1 Adipocytes: One of Several Potential Extrapancreatic Sites of GLP-1 Action", Endocrinology, 1994, vol., 135 No. 1, pp. 2070-2075.

M.L. Villanueva-Peñacarrillo, et al., "Potent glycogenic effect of GLP-1(7-36)amide in rat skeletal muscle", Diabetologia, 1994, vol. 37, pp. 1163-1166.

S. Efendić, et al., "Glucagon-Like Insulinotropic Peptide Has a Stronger Antidiabetogenic Effect than Glibenclamide", Digestion, vol. 54, pp. 392-393.

M. Anvari, et al., "Effects of GLP-1 on Gastric Emptying, Antropyloric Motility, and Transpyloric Flow in Response to a Nonnutrient Liquid", Digestive Diseases and Sciences, 1998, vol. 43, No. 6, pp. 1133-1140.

J. Holst, et al , "Inhibition of the Activity of Dipeptidyl-Peptidase IV as a Treatment for Type 2 Diabetes", Diabetes, 1998, vol. 47, pp. 1663-1670.

B. Balkan, et al , "Inhibition of dipeptidyl peptidase IV with NVP-DPP728 increases plasma GLP-1 (7-36 amide) concentrations and improves oral glucose tolerance in obese Zucker rats," Diabetologia, 1999, vol. 42, pp. 1324-1331.

M. V. Blazquez, et al., "Selective Decrease of CD26 Expression in T Cells From HIV-1-Infected Individuals", The Journal of Immunology, 1992, vol. 149, No. 9, pp. 3073-3077.

M. Subramanyam, et al., "Mechanism of HIV-1 Tat Induced Inhibition of Antigen-Specific T Cell Responsiveness", The Journal of Immunology, 1993, vol. 150, No. 6, pp. 2544-2553.

E. Schön, et al., "Dipeptidyl Peptidase IV in the Immune System—Effects of Specific Enzyme Inhibitors on Activity of Dipeptidyl Peptidase IV and Proliferation of Human Lymphocytes", Biological Chemistry Hoppe-Seyler, 1991, vol. 372, pp. 305-311.

T. Mattern, et al., "Expression of CD26 (Dipeptidyl Peptidase IV) on Resting and Activated Human T-Lymphocytes", Scandinavian Journal of Immunology, 1991, vol. 33, pp. 737-748.

E. Schön, et al., "Dipeptidyl Peptidase IV in Human T Lymphocytes—Impaired Induction of Interleukin 2 and Gamma Interferon Due to Specific Inhibition of Dipeptidyl Peptidase IV", Scandinavian Journal of Immunology, 1989, vol. 29, pp. 127-132.

J. Kameoka, et al., "Direct Association of Adenosine Deaminase with a T Cell Activation Antigen, CD26", Science, 1993, vol. 261, pp. 466-469.

F. Raynaud, et al., "Characterization of Specific Proteases Associated With the Surface of Human Skin Fibroblasts, and Their Modulation in Pathology", Journal of Cellular Physiology, 1992, vol. 151, pp. 378-385.

G. Vanhoof, et al., "Distribution of Proline-Specific Aminopeptidases in Human Tissues and Body Fluids", European Journal of Clinical Chemistry and Clinical Biochemistry, 1992, vol. 30, No. 6, pp. 333-338.

R. C. Johnson, et al., "Lung Endothelial Dipeptidyl Peptidase IV Is an Adhesion Molecule for Lung-metastatic Rat Breast and Prostate Carcinoma Cells", The Journal of Cell Biology, 1993, vol. 121, No. 6, pp. 1423-1432.

E. B. Villhauer, et al., "1-[[(3-Hydroxy-1-adamantylamino]acetyl]-2-cyano-(S)-pyrrolidine: A Potent, Selective, and Orally Bioavailable Dipeptidyl Peptidase IV Inhibitor with Antihyperglycemic Properties", Journal of Medical Chemistry, 2003, vol. 46, pp. 2774-2789.

H. Fukushima, et al., "Synthesis and structure-activity relationships of potent 3- or 4-substituted-2-cyanopyrrolidine dipeptidyl peptidase IV inhibitors", Bioorganic & Medicinal Chemistry, 2004, vol. 12, pp. 6053-6061.

E. W. Della, et al., "Synthesis of Bridgehead-Bridgehead Substituted Bicycloalkanes", Australian Journal of Chemistry, 1985, vol. 38, pp. 1705-1718.

C. A. Grob, et al., "283. Die Synthese von 4-substituierten Bicyclo[2.2.2]oct-1-yl-p-nitrobenzolsulfonaten", Helvetica Chimica Acta, 1979, vol. 62, pp. 2802-2817.

S. A. Ahmed, et al., "Enamine Chemistry. Part 26. Preparation of Substituted Adamantane-2,4-diones and Bicyclo[2.2.2]octan-2-ones", Journal of Chem. Soc., Perkin I, 1979, pp. 2180-2183.

K. Morita, et al., "A Novel Cyclization of 4-Acetyl-1-methoxy-1-cyclohexene to 4-Alkoxybicyclo[2.2.2]octan-2-ones", J. Org. Chem., 1966, vol. 31, pp. 229-232.

W. Seebacher, et al., "Structural Requirements for the Antiprotozoal Activity of 4-Aminobicyclo[2.2.2]octan-2-ols", Monatshefte für Chemie, 2006, vol. 137, pp. 471-482.

J. D. Roberts, et al., "Syntheses of Some 4-Substituted Bicyclo [2.2.2]octane-1-carboxylic Acids", J. Am. Chem. Soc., 1953, vol. 75, pp. 637-640.

* cited by examiner

METHOD FOR PRODUCING AMINOACETYLPYRROLIDINE-CARBONITRILE DERIVATIVE

TECHNICAL FIELD

The present invention relates to a method for producing an aminoacetylpyrrolidinecarbonitrile derivative which has a dipeptidyl peptidase IV (DPP-IV) inhibitory activity and is useful for the prevention and/or treatment of diseases in which DPP-IV is concerned such as type II diabetes mellitus.

BACKGROUND OF THE INVENTION

In recent years, a dipeptidyl peptidase IV (DPP-IV, hereinafter) inhibitor has been drawing attention as a therapeutic agent for diabetes mellitus (particularly type II diabetes mellitus), and a large number of derivatives having DPP-IV inhibitory action have been reported. Particularly, since aminoacetylpyrrolidinecarbonitrile derivatives show an excellent blood sugar lowering action, several compounds promising as antidiabetic agents have been reported. It is general that these aminoacetylpyrrolidinecarbonitrile derivatives are produced by allowing 1-(2-chloroacetyl)pyrrolidine-2-carbonitrile or 1-(2-bromoacetyl)pyrrolidine-2-carbonitrile to react with a corresponding amine in the presence of a base (Patent References 1 to 16).

On the other hand, as a production method which does not use 1-(2-chloroacetyl)pyrrolidine-2-carbonitrile or 1-(2-bromoacetyl)pyrrolidine-2-carbonitrile, a method has been disclosed in which an aminoacetylpyrrolidinecarboxamide derivative is produced and then an aminoacetylpyrrolidinecarbonitrile derivative is produced by carrying out a dehydration reaction (Patent References 10 to 13, Patent References 17 to 19). However, the Patent References 10 to 13 do not illustratively describe with regard to the synthesis method of an aminoacetylpyrrolidinecarbonitrile derivative through a dehydration reaction of an aminoacetylpyrrolidinecarboxamide derivative, and the Patent References 17 to 19 describe only an illustrative example of carrying out the dehydrating reaction using an intermediate in which a protecting group is introduced into an amino group.

Patent Reference 1: JP-T-2000-511559 (the term "JP-T" as used herein means a published Japanese translation of a PCT patent application)
Patent Reference 2: JP-T-2002-531547
Patent Reference 3: JP-A-2002-356471 (the term "JP-A" as used herein means an unexamined published Japanese patent application)
Patent Reference 4: JP-T-2004-500321
Patent Reference 5: JP-T-2005-529078
Patent Reference 6: JP-T-2004-503531
Patent Reference 7: US 2002/019339
Patent Reference 8: WO 04/099185 pamphlet
Patent Reference 9: WO 05/075421 pamphlet
Patent Reference 10: WO 02/38541 pamphlet
Patent Reference 11: WO 03/095425 pamphlet
Patent Reference 12: JP-A-2004-26820
Patent Reference 13: JP-A-2006-160733
Patent Reference 14: JP-A-2002-356472
Patent Reference 15: JP-A-2004-2367
Patent Reference 16: JP-A-2004-2368
Patent Reference 17: WO 03/057666 pamphlet
Patent Reference 18: WO 04/026822 pamphlet
Patent Reference 19: WO 06/043595 pamphlet

DISCLOSURE OF THE INVENTION

Problems that the Invention is to Solve

A safe and efficient method for producing an aminoacetylpyrrolidinecarbonitrile derivative which is useful as a DPP-IV inhibitor is in demand.

Means for Solving the Problems

As a result of carrying out extensive studies on the method for producing an aminoacetylpyrrolidinecarbonitrile derivative, the inventors have found a practical production method which can efficiently produce an object substance by suppressing side reactions in comparison with conventional methods, by allowing an acid to act on an aminoacetylpyrrolidinecarboxamide derivative and then allowing a dehydrating agent to act thereon, thus resulting in the accomplishment of the present invention.

That is, the present invention relates to
1) a method for producing an aminoacetylpyrrolidinecarbonitrile derivative represented by the formula (2):

[Chem. 2]

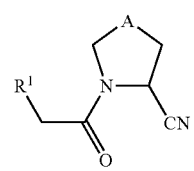

(2)

(in the formula, A and $R^1$ are as defined in the following), comprising
allowing an acid to act on an aminoacetylpyrrolidinecarboxamide derivative represented by the formula (1):

[Chem. 1]

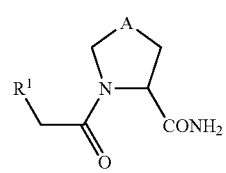

(1)

(in the formula, A represents $CH_2$, CHF or $CF_2$; and $R^1$ represents a secondary amino group which may be substituted); and
then allowing a dehydrating agent to act thereon;
2) the production method according to 1), wherein, in the formula (1) and formula (2), $R^1$ is a secondary amino group represented by the formula (3):

  (3)

(in the formula, $R^2$ represents a $C_1$-$C_6$ alkyl group which may be substituted, a $C_3$-$C_{10}$ cyclic alkyl group which may be substituted or a $C_2$-$C_{10}$ cyclic amino group which may be substituted);

3) a method for producing an aminoacetylpyrrolidinecarbonitrile derivative represented by the formula (5):

[Chem. 4]

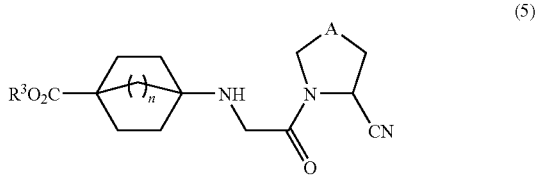

(5)

(in the formula, A, $R^3$ and n are as defined in the following), comprising allowing an acid to act on an aminoacetylpyrrolidinecarboxamide derivative represented by the formula (4):

[Chem. 3]

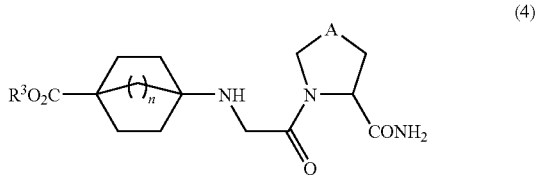

(4)

(in the formula, A represents $CH_2$, CHF or $CF_2$;
$R^3$ represents a $C_1$-$C_6$ alkyl group which may be substituted, a $C_3$-$C_8$ cycloalkyl group which may be substituted, an arylmethyl group which may be substituted, an arylethyl group which may be substituted, an aromatic hydrocarbon which may be substituted, an aromatic hereto ring which may be substituted, or an aliphatic hetero ring which may be substituted; and
n represents 1 or 2); and
then allowing a dehydrating agent to act thereon;
4) the production method according to 3), wherein, in the formula (4) and formula (5), A is CHF or $CF_2$ and $R^3$ is a $C_1$-$C_6$ alkyl group which may be substituted;
5) the production method according to 3), wherein, in the formula (4) and formula (5), A is CHF, $R^3$ is an ethyl group and n is 2;
6) the production method according to any one of 1) to 5), wherein the acid is a trihalogenoacetic acid, an arylsulfonic acid which may be substituted or a $C_1$-$C_3$ alkylsulfonic acid which may be substituted with one or more halogen atom(s);
7) the production method according to any one of 1) to 6), wherein the acid is trifluoroacetic acid, benzenesulfonic acid or 4-toluenesulfonic acid;
8) the production method according to any one of 1) to 7), wherein the dehydrating agent is a trihalogenoacetic anhydride or a $C_1$-$C_3$ alkylsulfonic anhydride which may be substituted with one or more halogen atom(s); and
9) the production method according to any one of 1) to 8), wherein the dehydrating agent is trifluoroacetic anhydride.

Effect of the Invention

An efficient and practical method for producing an aminoacetylpyrrolidinecarbonitrile derivative directly from an aminoacetylpyrrolidinecarboxamide derivative without carrying out protection and deprotection of an amino group, which had been unavoidable when a dehydrating agent is used alone, was established based on the effect of suppressing side reactions according to the present invention.

BEST MODE FOR CARRYING OUT THE INVENTION

The "secondary amino group which may be substituted" as shown in this description means a secondary amino group which may have 1 to 5 substituent groups selected from a halogen atom, a hydroxyl group, a cyano group, a $C_1$-$C_6$ alkoxy group, an aryloxy group which may be substituted, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group, a 4- to 9-membered cyclic amino group which may contain 1 to 3 hetero atoms, a formylamino group, a $C_1$-$C_6$ alkylcarbonylamino group, a $C_1$-$C_6$ alkoxycarbonylamino group, a $C_1$-$C_6$ alkylsulfonylamino group, and an arylsulfonylamino group which may be substituted;

wherein the "secondary amino group" means an aliphatic or aromatic amino group in which one hydrogen atom is substituted with the nitrogen atom located on the binding position with the acetylpyrrolidine skeleton, which means, for example, an amino group to which a $C_1$-$C_6$ alkyl group such as a methylamino group or a butylamino group is bonded, an amino group to which a $C_3$-$C_{10}$ cyclic alkyl group such as a cyclohexylamino group, an adamantylamino group or a bicyclo[2.2.2]octylamino group is bonded, an amino group to which a $C_2$-$C_{10}$ cyclic amino group such as a piperidylamino group or an azabicyclooctylamino group is bonded, an aromatic amino group (e.g., an anilyl group, a pyridylamino group and the like can be exemplified) and the like.

The "$C_1$-$C_6$ alkyl group which may be substituted" as shown in this description means a $C_1$-$C_6$ alkyl group which may have 1 to 5 substituent groups selected from a halogen atom, a hydroxyl group, a cyano group, a $C_1$-$C_6$ alkoxy group, an aryloxy group which may be substituted, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group, a 4- to 9-membered cyclic amino group which may contain 1 to 3 hetero atoms, a formylamino group, a $C_1$-$C_6$ alkylcarbonylamino group, a $C_1$-$C_6$ alkoxycarbonylamino group, a $C_1$-$C_6$ alkylsulfonylamino group, and an arylsulfonylamino group which may be substituted;

wherein the "$C_1$-$C_6$ alkyl group" means a straight chain or branched lower alkyl group, and for example, a methyl group, an ethyl group, a propyl group, a 1-methylethyl group, a 1-methylpropyl group, a 2-methylpropyl group, a 1-ethylpropyl group, a 2-ethylpropyl group, a butyl group, a hexyl group and the like can be cited.

The "$C_3$-$C_{10}$ cycloalkyl group which may be substituted" as shown in this description means a $C_3$-$C_{10}$ cycloalkyl group which may have 1 to 5 substituent groups selected from a halogen atom, a hydroxyl group, a cyano group, a $C_1$-$C_6$ alkoxy group, an aryloxy group which may be substituted, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group, a 4- to 9-membered cyclic amino group which may contain 1 to 3 hetero atoms, a formylamino group, a $C_1$-$C_6$ alkylcarbonylamino group, a $C_1$-$C_6$ alkoxycarbonylamino group, a $C_1$-$C_6$ alkylsulfonylamino group, and an arylsulfonylamino group which may be substituted;

wherein the "cycloalkyl group" means a $C_3$-$C_8$ cycloalkyl group, a $C_5$-$C_{10}$ bicycloalkyl group or an adamantyl group;

wherein the "$C_3$-$C_8$ cycloalkyl group" means an alkyl group which has a cycloalkyl ring, and for example, a cyclopropyl group, a cyclopropylmethyl group, a cyclobutyl group, a cyclopentyl group, a cyclohexyl group, a cycloheptyl group, a cyclooctyl group and the like can be cited; and the "$C_5$-$C_{10}$ bicycloalkyl group" means an alkyl group which has a bicycloalkyl ring, and for example, a bicyclopentyl group, a bicyclohexyl group, a bicyclopentyl group, a bicyclooctyl group, a bicyclononyl group, a bicyclodecyl group and the like can be cited.

The "$C_2$-$C_{10}$ cyclic amino group which may be substituted" as shown in this description means a $C_2$-$C_{10}$ cyclic amino group which may have 1 to 5 substituent groups selected from a halogen atom, a hydroxyl group, a cyano group, a $C_1$-$C_6$ alkoxy group, an aryloxy group which may be substituted, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group, a 4- to 9-membered cyclic amino group which may contain 1 to 3 hetero atoms, a formylamino group, a $C_1$-$C_6$ alkylcarbonylamino group, a $C_1$-$C_6$ alkoxycarbonylamino group, a $C_1$-$C_6$ alkylsulfonylamino group, and an arylsulfonylamino group which may be substituted;

wherein the "$C_2$-$C_{10}$ cyclic amino group" means a cyclic amino group which contains one or more nitrogen atoms in the ring and wherein an oxygen atom or sulfur atom may be present in the ring, and for example, an aziridyl group, a pyrrolidyl group, a piperidyl group, a morpholyl group, an oxazolyl group, an azabicycloheptyl group, an azabicyclooctyl group and the like can be cited.

The "$C_3$-$C_8$ cycloalkyl group which may be substituted" as shown in this description means a $C_3$-$C_8$ cycloalkyl group which may have 1 to 5 substituent groups selected from a halogen atom, a hydroxyl group, a cyano group, a $C_1$-$C_6$ alkoxy group, an aryloxy group which may be substituted, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group, a 4- to 9-membered cyclic amino group which may contain 1 to 3 hetero atoms, a formylamino group, a $C_1$-$C_6$ alkylcarbonylamino group, a $C_1$-$C_6$ alkoxycarbonylamino group, a $C_1$-$C_6$ alkylsulfonylamino group, and an arylsulfonylamino group which may be substituted;

wherein the "$C_3$-$C_8$ cycloalkyl group" means an alkyl group which has a cycloalkyl ring, and for example, a cyclopropyl group, a cyclopropylmethyl group, a cyclobutyl group, a cyclopentyl group, a cyclohexyl group, a cycloheptyl group, a cyclooctyl group and the like can be cited.

The "arylmethyl group which may be substituted" as shown in this description means an arylmethyl group which may have 1 to 5 substituent groups selected from a halogen atom, a $C_1$-$C_6$ alkyl group which may be substituted, a hydroxyl group, a cyano group, a nitro group, a $C_1$-$C_6$ alkoxy group which may be substituted, an aryloxy group which may be substituted, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group which may be substituted, an arylamino group which may be substituted, a 4- to 9-membered cyclic amino group which may contain 1 to 3 hetero atoms, a formylamino group, a $C_1$-$C_6$ alkylcarbonylamino group, a $C_1$-$C_6$ alkoxycarbonylamino group, a $C_1$-$C_6$ alkylsulfonylamino group and an arylsulfonylamino group which may be substituted (e.g., a phenylmethyl group, a naphthylmethyl group, a pyridylmethyl group, a quinolylmethyl group, an indolylmethyl group and the like can be cited).

The "arylethyl group which may be substituted" as shown in this description means an arylethyl group which may have 1 to 5 substituent groups selected from a halogen atom, a $C_1$-$C_6$ alkyl group which may be substituted, a hydroxyl group, a cyano group, a nitro group, a $C_1$-$C_6$ alkoxy group which may be substituted, an aryloxy group which may be substituted, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group which may be substituted, an arylamino group which may be substituted, 4- to 9-membered cyclic amino group which may contain 1 to 3 hetero atoms, a formylamino group, a $C_1$-$C_6$ alkylcarbonylamino group, a $C_1$-$C_6$ alkoxycarbonylamino group, a $C_1$-$C_6$ alkylsulfonylamino group and an arylsulfonylamino group which may be substituted (e.g., a phenylethyl group, a naphthylethyl group, a pyridylethyl group, a quinolylethyl group, an indolylethyl group and the like can be cited).

The "aromatic hydrocarbon which may be substituted" as shown in this description means an aromatic hydrocarbon which may have 1 to 5 substituent groups selected from a halogen atom, a hydroxyl group, a cyano group, a nitro group, a $C_1$-$C_6$ alkyl group which may be substituted, a $C_1$-$C_6$ alkoxy group, a $C_1$-$C_6$ alkylthio group and a $C_1$-$C_6$ dialkylamino group (e.g., a benzene ring, a naphthalene ring, an anthracene ring and the like can be cited).

The "aromatic hetero ring which may be substituted" as shown in this description means an aromatic hetero ring which may have 1 to 5 substituent groups selected from a halogen atom, a hydroxyl group, a cyano group, a nitro group, a $C_1$-$C_6$ alkyl group, a $C_1$-$C_6$ alkoxy group and a $C_1$-$C_6$ alkylthio group (a 5- or 6-membered aromatic monocyclic hetero ring or 9- or 10-membered aromatic condensed hetero ring which contains 1 to 3 hetero atoms optionally selected from a nitrogen atom, an oxygen atom and a sulfur atom, and for example, a pyridine ring, a pyrimidine ring, a pyridazine ring, a triazine ring, a quinoline ring, a naphthyridine ring, a quinazoline ring, an acridine ring, a pyrrole ring, a furan ring, a thiophene ring, an imidazole ring, a pyrazole ring, an oxazole ring, an isoxazole ring, a thiazole ring, an indole ring, a benzofuran ring, a benzothiazole ring, a benzimidazole ring, a benzoxazole ring and the like can be cited).

The "aliphatic hetero ring which may be substituted" as shown in this description means an aliphatic hetero ring which may have 1 to 5 substituent groups selected from a halogen atom, a $C_1$-$C_6$ alkyl group, a hydroxyl group, a cyano group, a nitro group, a $C_1$-$C_6$ alkoxy group and a $C_1$-$C_6$ alkylthio group (a 4- to 7-membered aliphatic monocyclic hetero ring or 9- or 10-membered aliphatic condensed hetero ring which contains 1 to 3 hetero atoms optionally selected from a nitrogen atom, an oxygen atom and a sulfur atom, and for example, a azetidine ring, a pyrrolidine ring, a tetrahydrofuran ring, a piperidine ring, a morpholine ring, a piperazine ring and the like can be cited).

The "acid" as shown in this description means an acid which can form a salt of the compound represented by the formula (1), which is soluble in a reaction solvent, and for example, it means a trihalogenoacetic acid such as trifluoroacetic acid, and trichloroacetic acid, or a sulfonic acid such as benzenesulfonic acid and 4-toluenesulfonic acid.

The "dehydrating agent" as shown in this description means a dehydrating agent which is generally used in a reaction for dehydrating an amido group into a nitrile group, and for example, acid anhydride such as carboxylic anhydride and sulfonic anhydride can be cited.

The "trihalogenoacetic acid" as shown in this description means, for example, trichloroacetic acid, trifluoroacetic acid or the like.

The "arylsulfonic acid which may be substituted" as shown in this description means, for example, benzenesulfonic acid, toluenesulfonic acid or the like.

The "$C_1$-$C_3$ alkylsulfonic acid which may be substituted with one or more halogen atom(s)" as shown in this description means, for example, methanesulfonic acid, trifluoromethanesulfonic acid or the like.

The "halogen atom" as shown in this description means a fluorine atom, a chlorine atom, a bromine atom or an iodine atom.

(Production Method)

[Chem. 5]

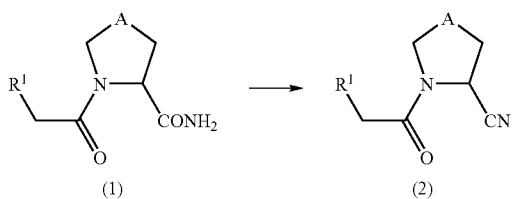

(In the formula, A and $R^1$ are as defined in the foregoing.)

According to the present invention, the aminoacetylpyrrolidinecarbonitrile derivative represented by the formula (2) can be obtained by allowing an acid to act on the aminoacetylpyrrolidinecarboxamide derivative represented by the formula (1) and then allowing a dehydrating agent to act thereon. In this case, regarding the method for adding the acid and the dehydrating agent, an acid may be added after dissolving a compound represented by the formula (1) in a reaction solvent, subsequently allowing a dehydrating agent to act thereon without isolation, or an acid may be allowed to act on a compound represented by the formula (1) to form a salt thereof, subsequently allowing a dehydrating agent to act thereon after isolating the salt.

As the acid, any acid may be used as long as it can form a salt with a compound represented by the formula (1) and the salt is soluble in a reaction solvent, and a trihalogenoacetic acid such as trifluoroacetic acid and trichloroacetic acid, and a sulfonic acid such as benzenesulfonic acid and 4-toluenesulfonic acid are preferable, of which trifluoroacetic acid or benzenesulfonic acid is particularly preferable. Its amount to be used is preferably 1 equivalent or more, particularly preferably from 1 to 1.2 equivalents, based on a compound represented by the formula (1).

As the dehydrating agent, a carboxylic anhydride and a sulfonic anhydride can be exemplified, and trihalogenoacetic anhydride such as trifluoroacetic anhydride and trichloroacetic anhydride, and alkylsulfonic anhydride which may be substituted with one or more halogen atom(s) such as methanesulfonic anhydride and trifluoromethanesulfonic anhydride are preferable, of which trifluoroacetic anhydride is particularly preferable. Its amount to be used is preferably 1 to 2 equivalents, particularly preferably from 1 to 1.2 equivalents, based on the aminoacetylpyrrolidinecarboxamide derivative represented by the formula (1).

As the reaction solvent, it may be any inert solvent which can dissolve therein a salt formed from a compound represented by the formula (1) and an acid to be added and does not participate in the reaction, and a chain amide type solvent such as N,N-dimethylformamide and N,N-dimethylacetamide or a cyclic amide type solvent such as N-methyl-2-pyrrolidinone is desirable, of which N,N-dimethylformamide or N,N-dimethylacetamide is more desirable and N,N-dimethylformamide is particularly desirable. The reaction can be carried out at from −30° C. to 50° C., preferably from −10° C. to 30° C., particularly preferably from 0° C. to 20° C.

In addition, the aminoacetylpyrrolidinecarboxamide derivative represented by the formula (1) as a material in the present invention can be produced, for example, by the following production method.

[Chem. 6]

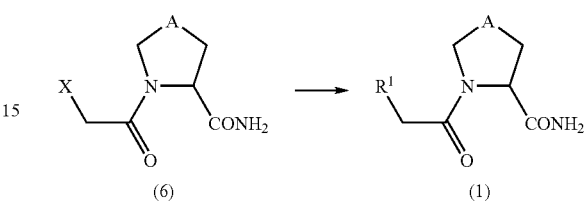

(In the formula, A and $R^1$ are as defined in the foregoing, and X represents a leaving group such as a chlorine atom, a bromine atom, a methanesulfonyloxy group, and a benzenesulfonyloxy group.)

That is, the aminoacetylpyrrolidinecarboxamide derivative represented by the formula (1) can be produced by allowing an acetylpyrrolidinecarboxamide derivative having a leaving group, represented by the formula (6), to react with an amine derivative or a salt thereof in the presence or absence of a base.

When a base is used in the above-mentioned reaction, an alkali carbonate such as sodium bicarbonate, potassium carbonate, and cesium carbonate, and tertiary amines such as triethylamine, N,N-diisopropylethylamine, N-methylmorpholine, pyridine, and 4-dimethylaminopyridine can be exemplified, of which potassium carbonate or triethylamine is preferable. When a catalyst is used in the above-mentioned reaction, a phase-transfer catalyst or an organic salt such as tetrabutylammonium bromide, tetrabutylammonium iodide, lithium bromide, lithium iodide, sodium iodide, and potassium iodide can be exemplified, of which potassium iodide is preferable. As the reaction solvent, an inert solvent which does not participate in the reaction such as acetone, tetrahydrofuran, dioxane, ethyl ether, dimethoxyethane, acetonitrile, ethyl acetate, toluene, xylene, dichloromethane, chloroform, N,N-dimethylformamide, N,N-dimethylacetamide, N-methyl-2-pyrrolidone and the like can be exemplified, of which N,N-dimethylformamide or acetonitrile is preferable. The above-mentioned reaction can be carried out at from 0 to 100° C., preferably from 0° C. to 60° C.

Examples

The following describes the present invention based on Examples, but the present invention is not limited to these Examples. In addition, a production method of the starting compound to be used in Examples was shown as Reference Example.

Reference Example

Synthesis of (2S,4S)-1-[2-[(4-ethoxycarbonylbicyclo[2.2.2]oct-1-yl)amino]acetyl]-4-fluoropyrrolidine-2-carboxamide Method A: Potassium carbonate (277 mg) was added to a solution of ethyl 4-aminobicyclo[2.2.2]octane-1-carboxylate hydrochloride (319 mg) in N,N-dimethylformamide (1.8 mL), followed by stirring at an inner temperature of 40° C. for 30 minutes. (2S,4S)-4-Fluoro-1-[2-(benzenesulfonyloxy) acetyl]pyrrolidine-2-carboxamide (295 mg) was added thereto, followed by stirring at the same temperature for 1 hour. Water (5.4 mL) was added to the reaction solution, followed by stirring at an inner temperature of from 5 to 10° C. for 30 minutes. The precipitate were collected by filtration, washed with cold water (4 mL) and then blast-dried at an outer temperature of 40° C., thereby obtaining white crystals of (2S,4S)-1-[2-[(4-ethoxycarbonylbicyclo[2.2.2]oct-1-yl) amino]acetyl]-4-fluoropyrrolidine-2-carboxamide (obtained amount: 247 mg, yield: 75%).

MS (ESI$^+$) m/z: 370 (M+H$^+$).
HRMS (ESI$^+$) for $C_{18}H_{28}FN_3O_4$:
calcd, 370.21421; found, 370.21842.

Method B: Ethyl 4-aminobicyclo[2.2.2]octane-1-carboxylate hydrochloride (68.8 g), potassium carbonate (77.6 g), potassium iodide (46.6 g) and N,N-dimethylformamide (167 mL) were mixed, and (2S,4S)-1-(chloroacetyl)-4-fluoropyrrolidine-2-carboxamide (55.8 g) was added dropwise thereto for 6 hours, while stirring at room temperature. After further stirring at the same temperature for 1 hour, water (1400 mL) was added to the reaction solution, followed by stirring at an inner temperature of 10° C. or lower for 1 hour. The precipitate were collected by filtration, washed with cold water (279 mL) and then dried under a reduced pressure at an outer temperature of 60° C., thereby obtaining white crystals of (2S,4S)-1-[2-[(4-ethoxycarbonylbicyclo[2.2.2]oct-1-yl) amino]acetyl]-4-fluoropyrrolidine-2-carboxamide (obtained amount: 72.9 g, yield: 74%).

Example 1

Synthesis of (2S,4S)-1-[2-[(4-ethoxycarbonylbicyclo [2.2.2]oct-1-yl)amino]acetyl]-4-fluoropyrrolidine-2-carbonitrile (synthesis method 1)

(2S,4S)-1-[2-[(4-Ethoxycarbonylbicyclo[2.2.2]oct-1-yl) amino]acetyl]-4-fluoropyrrolidine-2-carboxamide (3.70 g) was dissolved in N,N-dimethylformamide (18.5 mL), and while stirring under ice-cooling, trifluoroacetic acid (0.78 mL) was added thereto at an inner temperature of 10° C. or lower. After stirring at an inner temperature of from 0 to 10° C. for 10 minutes, trifluoroacetic anhydride (1.46 mL) was added dropwise thereto, followed by stirring at the same temperature for 1 hour. The reaction solution was poured into ice-water (92.5 mL), potassium carbonate (2.80 g) was added thereto in small portions at an inner temperature of 10° C. or lower and then, after gradually increasing the temperature, potassium carbonate (1.50 g) was further added thereto at an inner temperature of from 35 to 40° C. This was stirred at the same temperature for 10 minutes and then ice-cooled and stirred for 1 hour. The precipitate were collected by filtration, washed with water (37.0 mL) and then dried at 60° C. under reduced pressure, thereby obtaining a white powder of (2S,4S)-1-[2-[(4-ethoxycarbonylbicyclo[2.2.2]oct-1-yl)amino] acetyl]-4-fluoropyrrolidine-2-carbonitrile (obtained amount: 2.84 g, yield: 81%).

MS (ESI$^+$) m/z: 352 (M+H$^+$).
HRMS (ESI$^+$) for $C_{18}H_{28}FN_3O_4$: calcd, 352.20364, found, 352.20766.

Example 2

Synthesis of (2S,4S)-1-[2-[(4-ethoxycarbonylbicyclo [2.2.2]oct-1-yl)amino]acetyl]-4-fluoropyrrolidine-2-carbonitrile (synthesis method 2)

Using (2S,4S)-1-[2-[(4-ethoxycarbonylbicyclo[2.2.2]oct-1-yl)amino]acetyl]-4-fluoropyrrolidine-2-carboxamide (739 mg), trifluoroacetic anhydride (0.29 mL) as a dehydrating agent and trichloroacetic acid (327 mg) as an acid, a white powder of (2S,4S)-1-[2-[(4-ethoxycarbonylbicyclo[2.2.2] oct-1-yl)amino]acetyl]-4-fluoropyrrolidine-2-carbonitrile was obtained (obtained amount: 524 mg, yield: 75%) by the same method of Example 1.

Example 3

Synthesis of (2S,4S)-1-[2-[(4-ethoxycarbonylbicyclo [2.2.2]oct-1-yl)amino]acetyl]-4-fluoropyrrolidine-2-carbonitrile (synthesis method 3)

Using (2S,4S)-1-[2-[(4-ethoxycarbonylbicyclo[2.2.2]oct-1-yl)amino]acetyl]-4-fluoropyrrolidine-2-carboxamide (3.70 g), trichloroacetic anhydride (1.9 mL) as a dehydrating agent and trifluoroacetic acid (0.78 mL) as an acid, a white powder of (2S,4S)-1-[2-[(4-ethoxycarbonylbicyclo[2.2.2] oct-1-yl)amino]acetyl]-4-fluoropyrrolidine-2-carbonitrile was obtained (obtained amount: 2.86 g, yield: 81%) by the same method of Example 1.

Example 4

Synthesis of (2S,4S)-1-[2-[(4-ethoxycarbonylbicyclo [2.2.2]oct-1-yl)amino]acetyl]-4-fluoropyrrolidine-2-carbonitrile (synthesis method 4)

Using (2S,4S)-1-[2-[(4-ethoxycarbonylbicyclo[2.2.2]oct-1-yl)amino]acetyl]-4-fluoropyrrolidine-2-carboxamide (1.00 g), trifluoromethanesulfonic anhydride (0.50 mL) as a dehydrating agent and trifluoroacetic acid (0.23 mL) as an acid, a white powder of (2S,4S)-1-[2-[(4-ethoxycarbonylbicyclo[2.2.2]oct-1-yl)amino]acetyl]-4-fluoropyrrolidine-2-carbonitrile was obtained (obtained amount: 754 mg, yield: 79%) by the same method of Example 1.

Example 5

Synthesis of (2S,4S)-1-[2-[(4-ethoxycarbonylbicyclo [2.2.2]oct-1-yl)amino]acetyl]-4-fluoropyrrolidine-2-carbonitrile (synthesis method 5)

Using (2S,4S)-1-[2-[(4-ethoxycarbonylbicyclo[2.2.2]oct-1-yl)amino]acetyl]-4-fluoropyrrolidine-2-carboxamide (500 mg), methanesulfonic anhydride (248 mg) as a dehydrating agent and trifluoroacetic acid (0.11 mL) as an acid, a white powder of (2S,4S)-1-[2-[(4-ethoxycarbonylbicyclo[2.2.2] oct-1-yl)amino]acetyl]-4-fluoropyrrolidine-2-carbonitrile was obtained (obtained amount: 340 mg, yield: 71%) by the same method of Example 1.

Example 6

Synthesis of (2S,4S)-1-[2-[(4-ethoxycarbonylbicyclo [2.2.2]oct-1-yl)amino]acetyl]-4-fluoropyrrolidine-2-carbonitrile (synthesis method 6)

Step 1: Synthesis of (2S,4S)-1-[2-[(4-ethoxycarbonylbicyclo[2.2.2]oct-1-yl)amino]acetyl]-4-fluoropyrrolidine-2-carboxamide benzenesulfonate (2S,4S)-1-[2-[(4-Ethoxycarbonylbicyclo[2.2.2]oct-1-yl) amino]acetyl]-4-fluoropyrrolidine-2-carboxamide (1.00 g) was dissolved in dichloromethane (10 mL), and a suspension of benzenesulfonic acid monohydrate (500 mg) in dichloromethane-methanol (5:1, 6 mL) was added thereto, followed by stirring at room temperature for 3 hours. The precipitate were collected by filtration, washed with dichloromethane (5 mL) and then dried, thereby obtaining a colorless solid of (2S,4S)-1-[2-[(4-ethoxycarbonylbicyclo[2.2.2]oct-1-yl) amino]acetyl]-4-fluoropyrrolidine-2-carboxamide benzenesulfonate (1.15 g, yield: 81%).
Elemental analysis (%): for $C_{18}H_{28}FN_3O_4 \cdot C_6H_6O_3S$
Calcd: C, 54.63; H, 6.50; N, 7.96
Found: C, 54.42; H, 6.39; N, 8.03

Step 2: Synthesis of (2S,4S)-1-[2-[(4-ethoxycarbonylbicyclo[2.2.2]oct-1-yl)amino]acetyl]-4-fluoropyrrolidine-2-carbonitrile (2S,4S)-1-[2-[(4-Ethoxycarbonylbicyclo[2.2.2]-oct-1-yl) amino]acetyl]-4-fluoropyrrolidine-2-carboxamide benzenesulfonate (791 mg) was suspended in N,N-dimethylformamide (2.8 mL), and trifluoroacetic acid anhydride (0.22 mL) was added thereto, followed by stirring under ice-cooling for 1 hour. After adding water (14 mL), potassium carbonate (644 mg) was added thereto at a bath temperature of 40° C., followed by ice-cooling and 1 hour of stirring. The precipitate were collected by filtration, washed with water (3 mL) and then blast-dried at 60° C., thereby obtaining a white powder of (2S,4S)-1-[2-[(4-ethoxycarbonylbicyclo[2.2.2]oct-1-yl) amino]acetyl]-4-fluoropyrrolidine-2-carbonitrile (441 mg, 84%).

Example 7

Synthesis of (2S,4S)-1-[2-[(4-ethoxycarbonylbicyclo [2.2.2]oct-1-yl)amino]acetyl]-4-fluoropyrrolidine-2-carbonitrile (synthesis method 7)

Step 1: Synthesis of (2S,4S)-1-[2-[(4-ethoxycarbonylbicyclo[2.2.2]oct-1-yl)amino]acetyl]-4-fluoropyrrolidine-2-carboxamide 4-toluenesulfonate (2S,4S)-1-[2-[(4-Ethoxycarbonylbicyclo[2.2.2]-oct-1-yl) amino]acetyl]-4-fluoropyrrolidine-2-carboxamide (1.00 g) was dissolved in 2-propanol (10 mL) with heating, and a solution of 4-toluenesulfonic acid monohydrate (541 mg) in 2-propanol (4 mL) was added thereto. After ice-cooling and subsequent 1 hour of stirring, the precipitate were collected by filtration, washed with 2-propanol (5 mL) and then blast-dried at 60° C., thereby obtaining a colorless solid of (2S,4S)-1-[2-[(4-ethoxycarbonylbicyclo[2.2.2]-oct-1-yl)amino] acetyl]-4-fluoropyrrolidine-2-carboxamide 4-toluenesulfonate (1.28 g, yield: 88%).
Elemental analysis (%): for $C_{18}H_{28}FN_3O_4 \cdot C_7H_8O_3S$
Calcd: C, 55.44; H, 6.70; N, 7.76
Found: C, 55.16; H, 6.65; N, 7.75

Step 2: Synthesis of (2S,4S)-1-[2-[(4-ethoxycarbonylbicyclo[2.2.2]oct-1-yl)amino]acetyl]-4-fluoropyrrolidine-2-carbonitrile Using (2S,4S)-1-[2-[(4-ethoxycarbonylbicyclo[2.2.2]oct-1-yl)amino]acetyl]-4-fluoropyrrolidine-2-carboxamide 4-toluenesulfonate (812 mg), a white powder of (2S,4S)-1-[2-[(4-ethoxycarbonylbicyclo[2.2.2]oct-1-yl)amino]acetyl]-4-fluoropyrrolidine-2-carbonitrile (391 mg, yield: 74%) was obtained by the same method of Step 2 in Example 6.

Comparative Test Example

As for the dehydration reaction of (2S,4S)-1-[2-[(4-ethoxycarbonylbicyclo[2.2.2]oct-1-yl)amino]acetyl]-4-fluoropyrrolidine-2-carboxamide which is an aminoacetylpyrrolidinecarboxamide derivative represented by the formula (1), the following shows a comparison result of a production method of a case of using a dehydrating agent alone and that of a case of using a dehydrating agent and an acid. The comparative example in the following table was carried out in the same manner as the case of Example 1, except that trifluoroacetic acid as the acid was not added. In addition, each formation ratio was calculated by measuring peak strength ratio by HPLC.

TABLE 1

[Structures showing the reaction: Desired compound and N-acyl form, where R in the acyl group is derived from anhydride]

| | Acid anhydride (eq.) | Acid (eq.) | Reaction time (h) | Desired compound: N-acyl form |
|---|---|---|---|---|
| Comp. Ex. | $(CF_3CO)_2O$ (1.05) | none | 1 | 20:1 |
| Example 1 | $(CF_3CO)_2O$ (1.05) | $CF_3CO_2H$ (1.0) | 1 | 217:1 |
| Example 3 | $(CCl_3CO)_2O$ (1.05) | $CF_3CO_2H$ (1.0) | 3 | N-acyl form was not detected |
| Example 6 | $(CF_3CO)_2O$ (1.05) | $PhSO_3H$ (1.0)* | 1 | N-acyl form was not detected |
| Example 7 | $(CF_3CO)_2O$ (1.05) | 4-Me-$PhSO_3H$ (1.0)* | 1 | N-acyl form was not detected |

*In Examples 6 and 7, salt was isolated and then used in the reaction.
**HPLC measuring conditions:
Detector: Ultraviolet absorptiometer (measuring wavelength: 205 nm)
Column: Inertsil ODS-3 (trade name: GL Science Inc.), 4.6 mm in inner diameter × 15 cm in length
Guard column: Inertsil ODS-3 (trade name: GL Science Inc.), 4.0 mm in inner diameter × 10 mm in length
Column temperature: 30° C.
Mobile phase: A 0.1% phosphoric acid aqueous solution containing 5 mmol/liter of sodium 1-octanesulfonate is used as a Liquid A, and acetonitrile for liquid chromatography is used as a Liquid B. Liquid A:Liquid B = 66:34
Flow rate: 1.0 mL/min As shown in the table, in the case of the methods described in the already reported Patent References 10 to 13 or Patent References 17 to 19 (comparative example), considerable amount of by-product of N-acyl form was found when the acetyl group-substituted amino group has no protecting group. However, it was found that side reactions are significantly suppressed by the method of the present invention in which an acid is added in advance or a dehydrating agent is allowed to act thereon after forming a salt.

That is, the method of the present invention can suppress side reactions without introducing a protecting group and therefore is a practical method for efficiently producing an aminoacetylpyrrolidinecarbonitrile derivative, in comparison with the conventional methods.

INDUSTRIAL APPLICABILITY

An efficient and practical method for producing an aminoacetylpyrrolidinecarbonitrile derivative represented by the formula (2), which is useful as a DPP-IV inhibitor, can be provided by the present invention, which therefore is industrially useful.

The invention claimed is:

1. A method for producing an aminoacetylpyrrolidinecarbonitrile derivative represented by the formula (2):

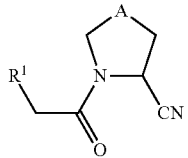

(2)

comprising
allowing an acid to act on an aminoacetylpyrrolidinecarboxamide derivative represented by the formula (1) to form a salt

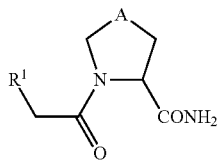

(1)

wherein A represents $CH_2$, CHF or $CF_2$; and
$R^1$ represents a secondary amino group of the formula (3):

$R^2$—NH— (3)

wherein $R^2$ represents a $C_1$-$C_6$ alkyl group which may be substituted, a $C_3$-$C_{10}$ cyclic alkyl group which may be substituted or a $C_2$-$C_{10}$ cyclic amino group which may be substituted, and the substituents for the $C_1$-$C_6$ alkyl group, $C_3$-$C_{10}$ cyclic alkyl group and $C_2$-$C_{10}$ cyclic amino group are selected from a halogen atom, a hydroxyl group, a cyano group, a $C_1$-$C_6$ alkoxy group, an aryloxy group which may be substituted, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group, a 4- to 9-membered cyclic amino group which may contain 1 to 3 hetero atoms, a formylamino group, a $C_1$-$C_6$ alkylcarbonylamino group, a $C_1$-$C_6$ alkoxycarbonylamino group, a $C_1$-$C_6$ alkylsulfonylamino group, and an arylsulfonylamino group which may be substituted; and
then allowing a dehydrating agent to act on the salt,
wherein the acid is a trihalogenoacetic acid, an arylsulfonic acid which may be substituted or a $C_1$-$C_3$ alkylsulfonic acid which may be substituted with one or more halogen atom(s).

2. A method for producing an aminoacetylpyrrolidinecarbonitrile derivative represented by the formula (5):

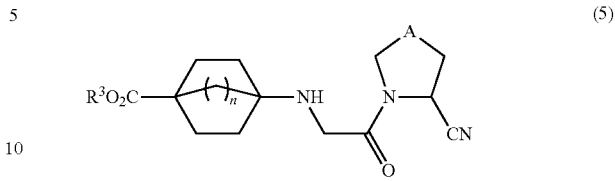

(5)

comprising
allowing an acid to act on an aminoacetylpyrrolidinecarboxamide derivative represented by the formula (4):

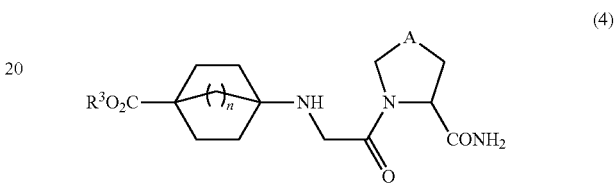

(4)

wherein A represents $CH_2$, CHF or $CF_2$;
$R^3$ represents a $C_1$-$C_6$ alkyl group which may be substituted, a $C_3$-$C_8$ cycloalkyl group which may be substituted, an arylmethyl group which may be substituted, an arylethyl group which may be substituted, an aromatic hydrocarbon which may be substituted, an aromatic hetero ring which may be substituted, or an aliphatic hetero ring which may be substituted; and
n represents 1 or 2; and
then allowing a dehydrating agent to act thereon,
wherein the acid is a trihalogenoacetic acid, an arylsulfonic acid which may be substituted or a $C_1$-$C_3$ alkylsulfonic acid which may be substituted with one or more halogen atom(s).

3. The production method according to claim 2, wherein, in the formula (4) and formula (5), A is CHF or $CF_2$ and $R^3$ is a $C_1$-$C_6$ alkyl group which may be substituted.

4. The production method according to claim 2, wherein, in the formula (4) and formula (5), A is CHF, $R^3$ is an ethyl group and n is 2.

5. The production method according to claim 1, wherein the acid is trifluoroacetic acid, benzenesulfonic acid or 4-toluenesulfonic acid.

6. The production method according to claim 1, wherein the dehydrating agent is a trihalogenoacetic anhydride or a $C_1$-$C_3$ alkylsulfonic anhydride which may be substituted with one or more halogen atom(s).

7. The production method according to claim 1, wherein the dehydrating agent is trifluoroacetic anhydride.

8. The production method according to claim 2, wherein the acid is trifluoroacetic acid, benzenesulfonic acid or 4-toluenesulfonic acid.

9. The production method according to claim 2, wherein the dehydrating agent is a trihalogenoacetic anhydride or a $C_1$-$C_3$ alkylsulfonic anhydride which may be substituted with one or more halogen atom(s).

10. The production method according to claim 2, wherein the dehydrating agent is trifluoroacetic anhydride.

* * * * *